United States Patent
Hansen

(10) Patent No.: US 10,064,724 B2
(45) Date of Patent: Sep. 4, 2018

(54) EXTERNAL BONE ANCHOR SYSTEM FOR JOINT REPLACEMENT IMPLANTS

(71) Applicant: Richard J Hansen, Eagan, MN (US)

(72) Inventor: Richard J Hansen, Eagan, MN (US)

(\*) Notice: Subject to any disclaimer, the term of this patent is extended or adjusted under 35 U.S.C. 154(b) by 0 days.

(21) Appl. No.: 14/823,355

(22) Filed: Aug. 11, 2015

(65) Prior Publication Data

US 2017/0042683 A1 Feb. 16, 2017

(51) Int. Cl.
*A61F 2/38* (2006.01)
*A61F 2/30* (2006.01)
*A61F 2/32* (2006.01)
*A61F 2/36* (2006.01)

(52) U.S. Cl.
CPC .......... *A61F 2/30* (2013.01); *A61F 2/32* (2013.01); *A61F 2/36* (2013.01); *A61F 2/38* (2013.01); *A61F 2/389* (2013.01); *A61F 2/3859* (2013.01); *A61F 2002/3038* (2013.01); *A61F 2002/30578* (2013.01); *A61F 2002/30909* (2013.01)

(58) Field of Classification Search
CPC .......... A61F 2/389; A61F 2/30907; A61F 2002/30909
See application file for complete search history.

(56) References Cited

U.S. PATENT DOCUMENTS

| | | | |
|---|---|---|---|
| 4,246,660 A | * | 1/1981 | Wevers ............... A61F 2/08 403/111 |
| 6,716,234 B2 | | 4/2004 | Grafton et al. |
| 7,029,490 B2 | | 4/2006 | Grafton et al. |
| 7,147,651 B2 | | 12/2006 | Morrison et al. |
| 7,326,222 B2 | | 2/2008 | Dreyfuss et al. |
| 8,092,545 B2 | | 1/2012 | Coon et al. |
| 8,109,969 B1 | | 2/2012 | Green et al. |
| 8,114,127 B2 | | 2/2012 | West, Jr. |
| 8,337,564 B2 | | 12/2012 | Shah et al. |
| 8,808,391 B2 | | 8/2014 | Mcminn |
| 9,005,246 B2 | | 4/2015 | Burkhart et al. |
| 2011/0213467 A1 | * | 9/2011 | Lozier ............... A61F 2/3607 623/20.32 |
| 2011/0224791 A1 | * | 9/2011 | Hodorek ............ A61F 2/30749 623/14.12 |
| 2012/0253414 A1 | | 10/2012 | Gabriel et al. |

\* cited by examiner

*Primary Examiner* — Brian Dukert
(74) *Attorney, Agent, or Firm* — Billlion & Armitage; John F. Klos

(57) ABSTRACT

A device for strengthening new joints in animals after joint replacement surgery includes a flexible bone anchor that connects to the new implant material on one end and to cortical bone on the other end.

8 Claims, 8 Drawing Sheets

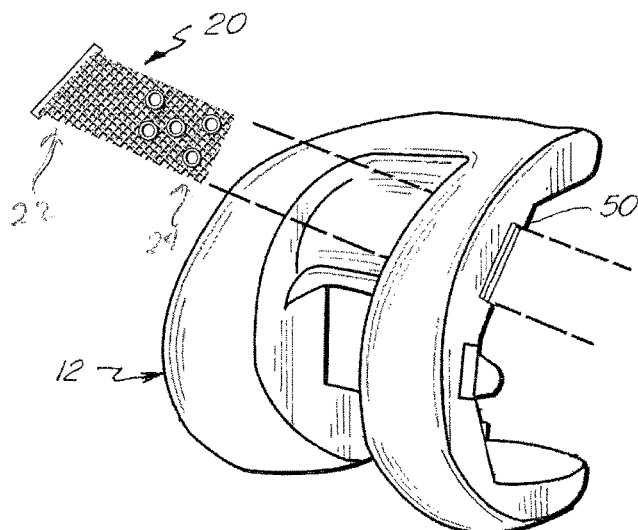
*Fig.3*
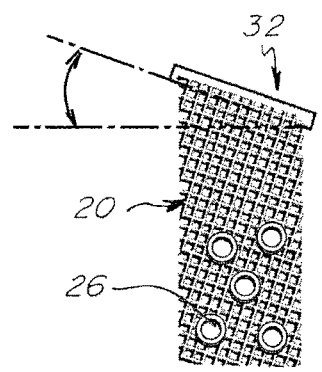
*Fig.4*
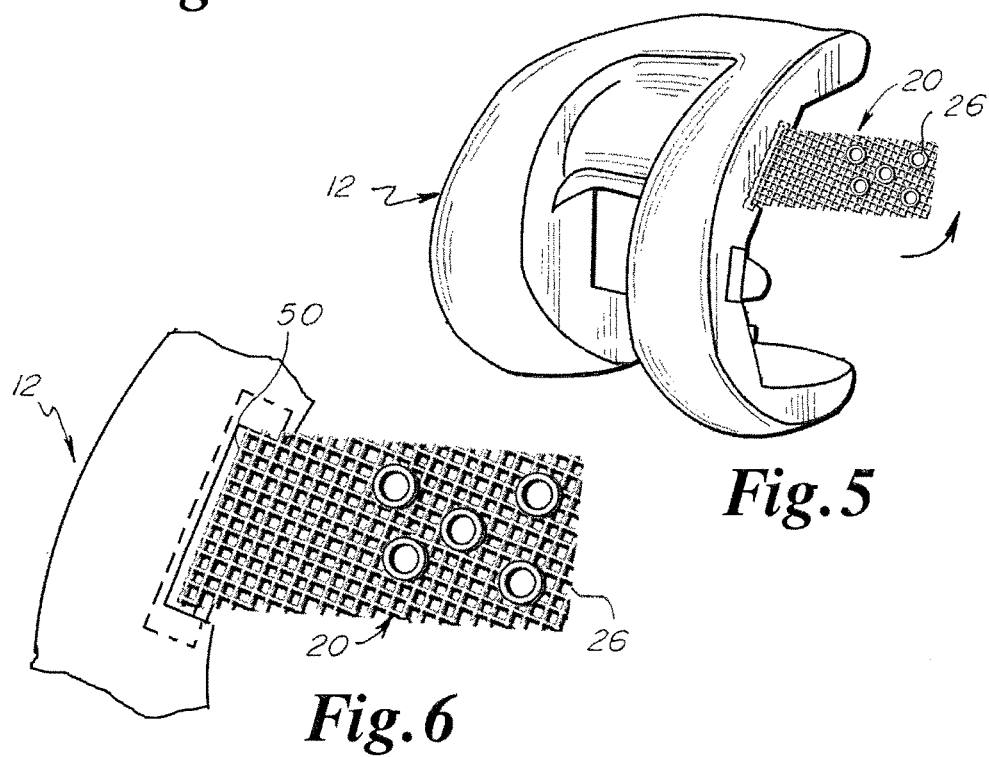
*Fig.5*
*Fig.6*

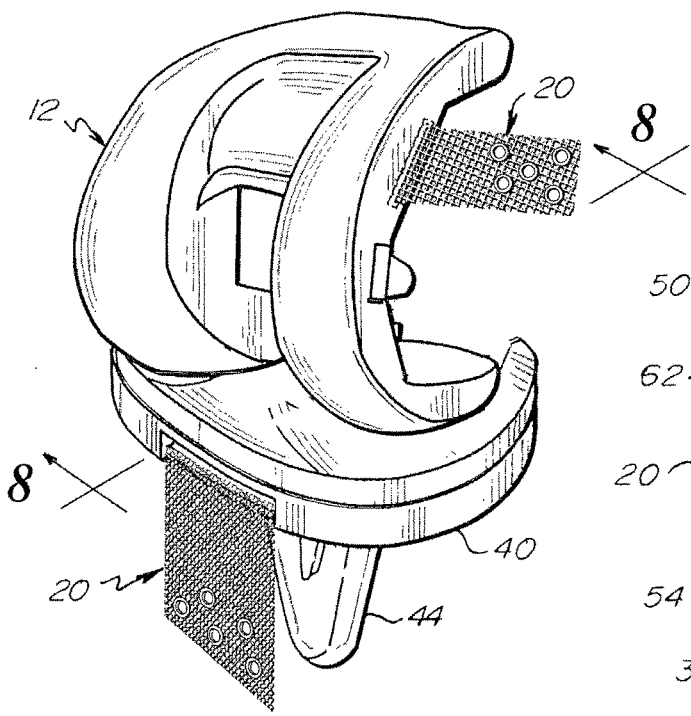
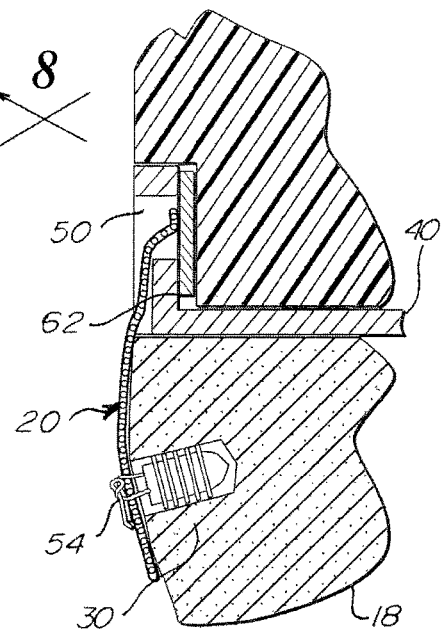
Fig. 7  Fig. 8
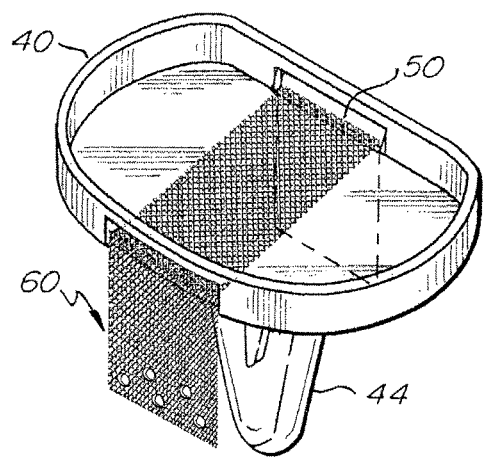
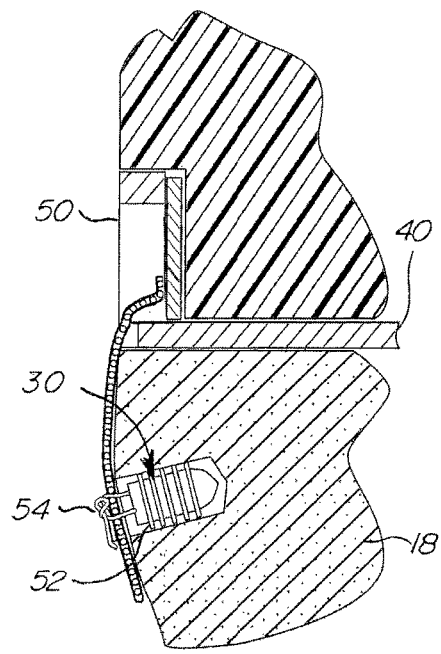
Fig. 9  Fig. 10

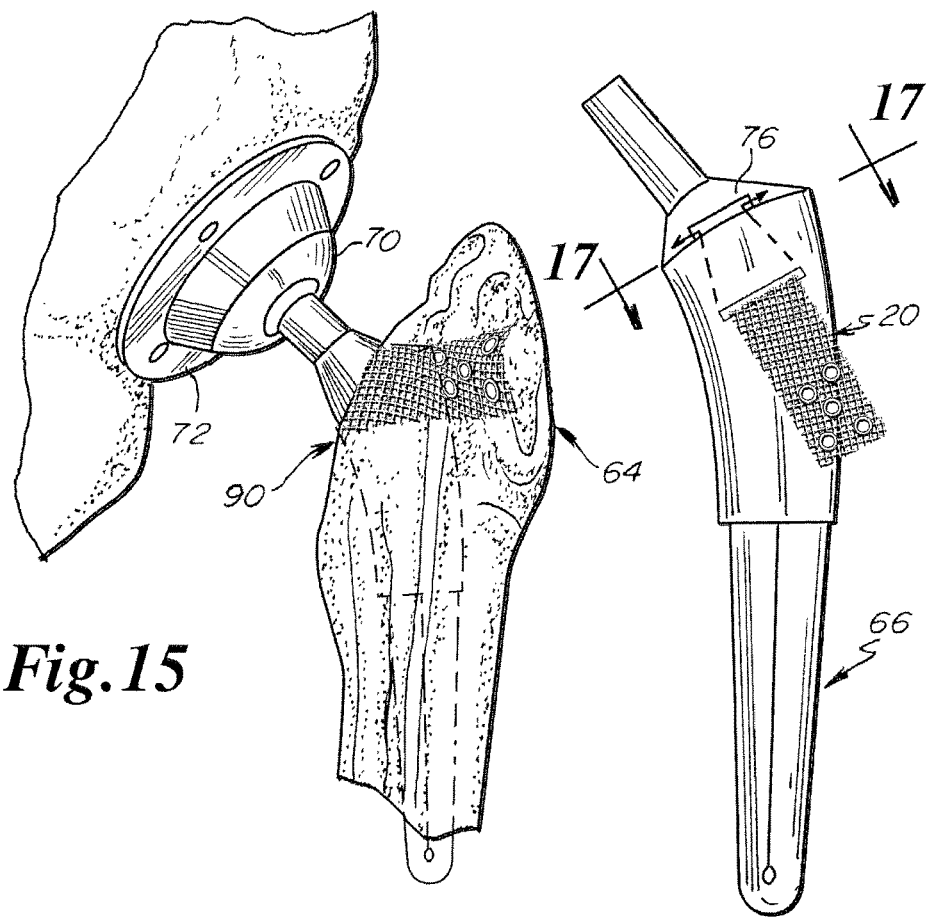
Fig.15
Fig.16
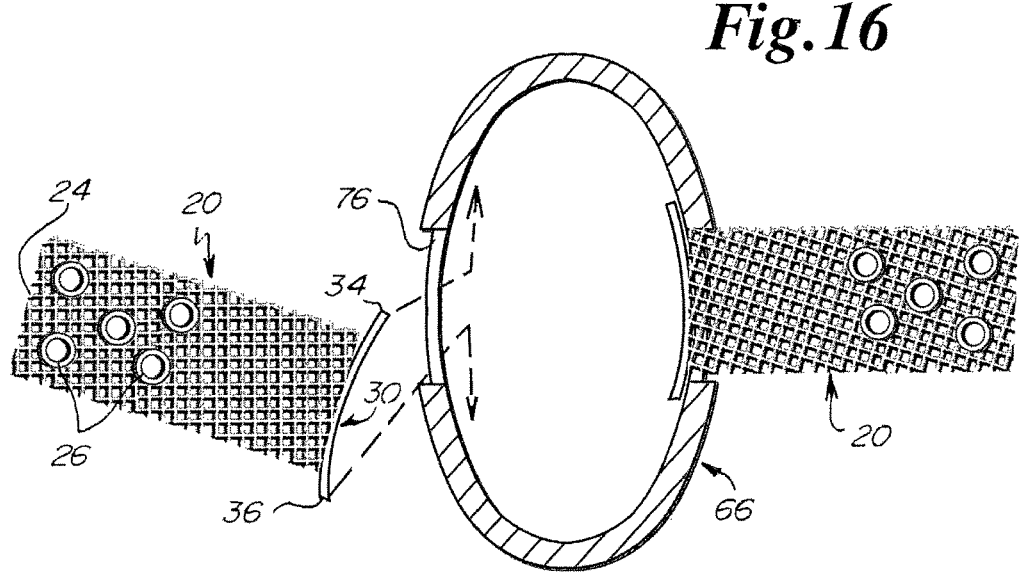
Fig.17

EXTERNAL BONE ANCHOR SYSTEM FOR JOINT REPLACEMENT IMPLANTS

CROSS-REFERENCE TO RELATED APPLICATIONS

None.

STATEMENT REGARDING FEDERALLY SPONSORED RESEARCH

Not Applicable

BACKGROUND OF THE INVENTION

Field of the Invention

This invention is directed toward apparatus and methods for treating joints and in particular, to treating hip joints and knee joints.

Description of the Related Art

U.S. Pat. No. 8,808,391 is an example of current hip joint prostheses U.S. Patent Publication No. 20120253414 A1 describes improvements in hip joint surgery in which a rail component is attached to the pelvis and a follower is attached to the femur to control load on the hip joint.

U.S. Pat. No. 8,337,564 is an example of a total knee replacement prosthesis. It includes a femoral component that connects to the distal end of a resected femur and a tibial component that connects to the proximal end of a resected tibia

BRIEF SUMMARY OF THE INVENTION

Hip joint and knee joint replacements are very common surgeries with excellent outcomes. In a hip joint replacement, a femoral implant is inserted into a cavity formed in the resected femur by removal of trabecular (spongy) bone. The hip socket (acetabulum)s is rebuilt with a metal or plastic cup. Generally, screws are not used in securing the femoral implant such that its rigidity is due to a close fit into the bore formed in the spongy bone. U.S. Pat. No. 8,808,391 which shows a typical hip replacement is incorporated herein by reference.

In a knee joint replacement, either a partial or total replacement is made. The surgery involves exposure of the front of the knee. The patella is displaced allowing exposure of the distal end of the femur and the proximal end of the tibia. The ends of these bones are then cut to shape. A round ended implant is used for the femur to form the natural shape of the joint. The tibial component is flat, but may have a stem down into the bone for further stability. A flattened or slightly dished high density polyethylene surface is inserted onto the tibial component. The weight is transferred metal to plastic not metal to metal. The fixation to bone is often with bone cement. Typical knee joint prostheses may be seen in U.S. Pat. Nos. 8,092,545 and 8,337,564, the disclosures of which are incorporated herein by reference.

In joint implants such as the hip and knee replacements noted above there is a reliance on securing the implants to spongy bone. This invention aims to improve the strength of the new implants by securing the implants to cortical bone in addition to the spongy bone. Briefly, a flexible bone anchor is used having two ends, one of which is affixed to the new implant and the other end is attached to the cortical bone by soft tissue anchors since traditional screws may loosen over time.

The flexibility of the titanium bone anchor allows it to tightly conform to the anatomy of the implant and the cortical bone where it is attached. The cortical bone, being harder and stronger helps to create a stronger implant since each component so attached is no longer attached to only spongy bone.

BRIEF DESCRIPTION OF THE SEVERAL VIEWS OF THE DRAWINGS

FIG. 3 is a side view of the femoral implant component showing the flexible bone anchor passing therein;

FIG. 4 is a view of the flexible bone anchor with an angled end;

FIG. 5 is a view similar to FIG. 3 in which the flexible bone anchor has passed through and locked to the femoral implant component;

FIG. 6 is an enlarged view of the locked in place flexible bone anchor of FIG. 5;

FIG. 7 is view of the total knee implant with two flexible bone anchors of the invention secured to the implant components;

FIG. 8 is a side sectional view from FIG. 7 showing the flexible bone anchor in relation to the femoral component and the resected femur;

FIG. 9 is a view of a tibial implant component with the flexible bone anchor passing there through;

FIG. 10 is a side sectional view from FIG. 7 showing the flexible bone anchor in relation to the tibial implant component and the resected tibia;

FIG. 15 is a view of a total hip replacement implant with a flexible bone anchor secured to the femoral bone and the implant;

FIG. 16 is a view of the hip stem as shown in FIG. 15 without the femur to show the connection to the flexible bone anchor;

FIG. 17 is a cross-sectional view through lines 17-17 of FIG. 16 showing two flexible bone anchors are secured to the hip stem;

DETAILED DESCRIPTION OF THE INVENTION

Figure 1:
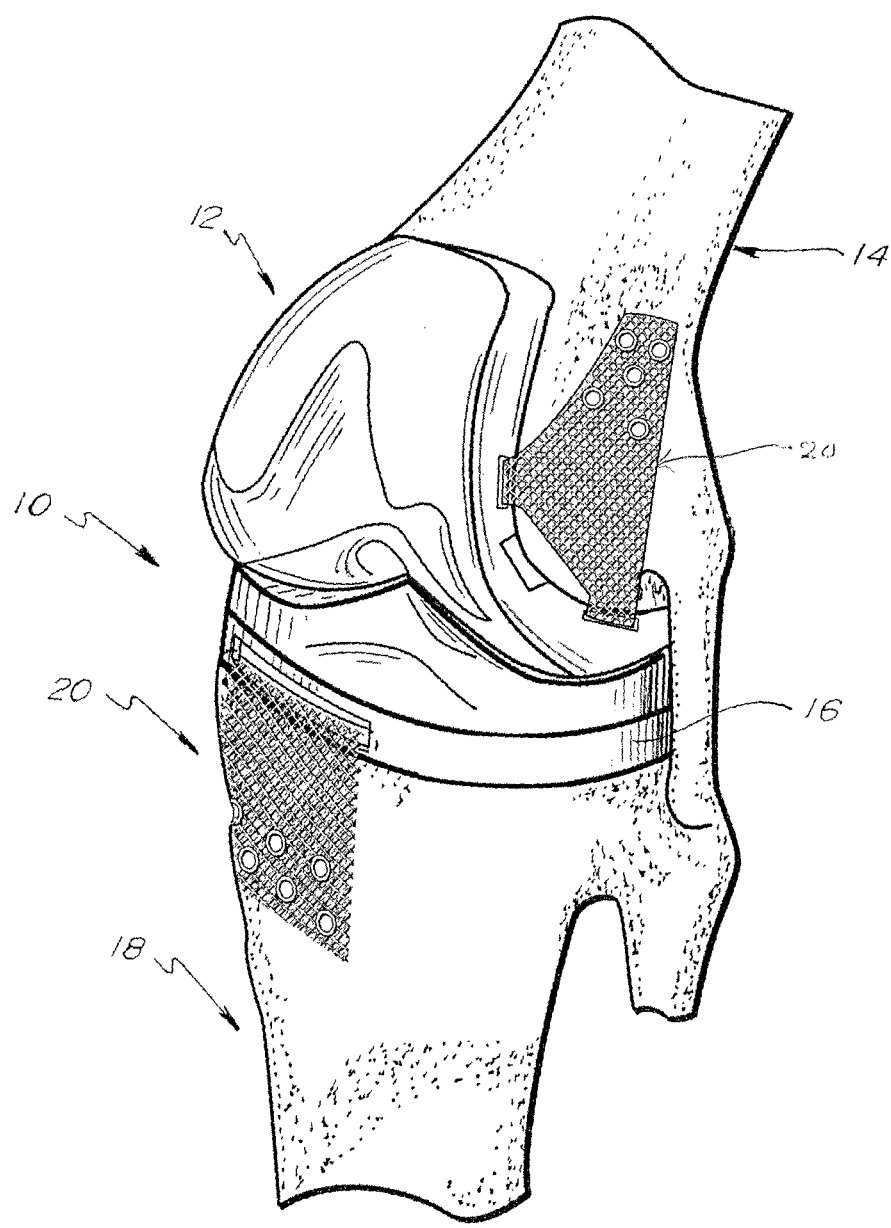
FIG. 1 is a perspective view of a total knee replacement implant with the external bone anchor system of the invention secured to a patient.

While this invention may be embodied in many different forms, there are shown in the drawings and described in detail herein specific preferred embodiments of the invention. The present disclosure is an exemplification of the principles of the invention and is not intended to limit the invention to the particular embodiments illustrated.

FIGS. 1-14 concern a total knee replacement implant 10 which is shown as including a femoral implant component 12 attached to a resected femur 14 and a tibial implant component 16 attached to a resected tibia 18. The femoral implant component 12 and tibial implant component 16 will vary according to the manufacturer and are illustrated to show typical components in a total knee replacement.

The inventive flexible external bone anchors of the invention are shown as a flexible bone anchor 20 attached to the new implants at one end and at the other end to cortical bone of the femur and tibia. As shown in the figures, the flexible bone anchor 20 is constructed generally as a rectangular strip having an implant connection end 22 and a cortical bone connection end 24.

The flexible bone anchor 20 may be formed from titanium for strength and compatibility in the body after implantation. It is relatively thin since it is not providing the primary connection for the new joint but is assisting the structure, stability and strength of the new joint. The flexible bone anchor 20 may be formed as a literal mesh which would impart good flexibility or it may have sufficient flexibility simply because of the thin titanium sheet.

Alternatively, the flexible bone anchor 20 may be formed from woven non-absorbable suture material such as Fiberwire® brand braided composite suture material from Arthrex, Inc. as found in U.S. Pat. Nos. 6,716,234; 7,029,490; 7,147,651; and 7,326,222, the disclosures of which are incorporated herein by reference. A generally rectangular woven mesh of such suture material can readily provide the same flexible structure as a titanium mesh. The implant connection end would need to have an attached enlarged rigid structure 32 such that the flexible bone anchor formed largely from woven suture material would have a rigid end for securely attaching to an implant.

Figure 20:
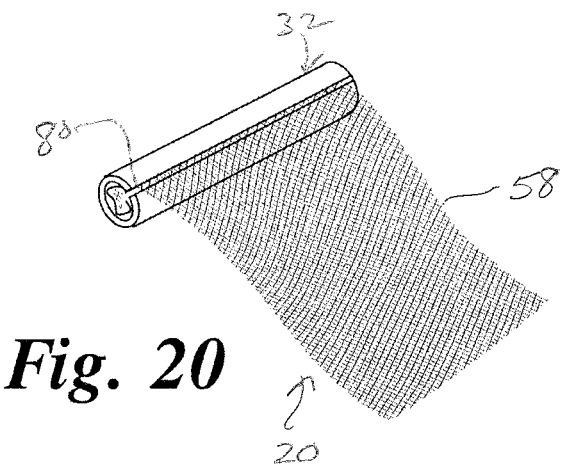
FIG. 20 shows a flexible bone anchor formed with suture material.
Figure 21:
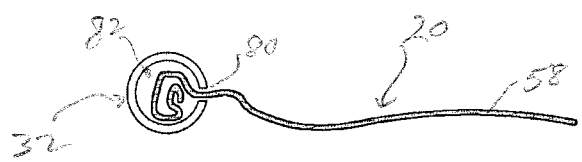
FIG. 21 shows the flexible bone anchor of FIG. 20 in a side view.

FIGS. 20-21 show forms in which the flexible bone anchor 20 is formed from a woven non-absorbable suture material 58. The attachment of the woven non-absorbent suture material 58 to the enlarged rigid structure 32 is not as simple as when both structures are titanium where they may be formed together or otherwise connected by known methods of connecting titanium to titanium. One such method is to include a slot 80 into which the implant connection end 22 of the flexible bone anchor 20 may be inserted. As shown, the end of the woven non-absorbable suture material 58 may be rolled up and slid through an end and slot 80 into a cavity 82 in the enlarged rigid structure 32 such that once so inserted it cannot come loose. The end may also be woven or otherwise secured into an enlarged end to be captured in cavity 82.

Figure 22:
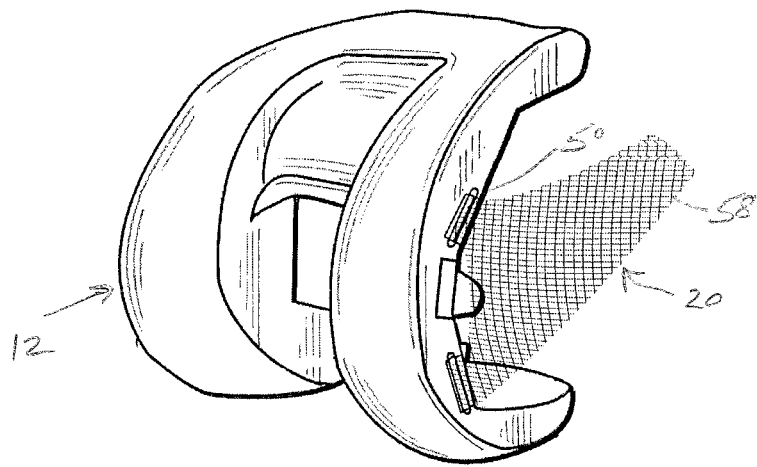
FIG. 22 shows a view similar to FIG. 3 showing an alternative connection point to the implant.

FIG. 22 shows the flexible bone anchor 20 formed with woven suture material 58 attached to a femoral implant component 12 in slots 50 via enlarged rigid structures 32. With woven non-absorbent suture material 58 the attachment of soft tissue bone anchors 30 may require a button device to spread forces through the woven fabric since simply running suture material of the soft tissue bone anchor 32 through an opening in the weave of the woven suture material 58 may not impart enough strength.

The cortical bone connection end 24 of the flexible bone anchor 20 may include a plurality of formed openings 26 through which soft tissue bone anchors 30 may be attached and secured into cortical bone. Alternatively, if the flexible bone anchor 20 is formed from a mesh, the mesh itself may form adequate openings through which the soft tissue bone anchors 30 may be secured. It is anticipated that when a flexible bone anchor formed from woven suture material that buttons may be needed in attaching the soft tissue bone anchors to the formed openings which would help spread the forces on the soft tissue anchor 30 to more than just an immediate suture of the woven suture material.

The implant connection end 22 is shown with an enlarged rigid structure 32 which extends beyond the width of the main body of the flexible bone anchor 20 such that it includes two tabs 34, 36. The enlarged rigid structure 32 may be formed integrally with the remainder of the flexible bone anchor 20 or may be added and permanently secured thereto.

Figure 2:
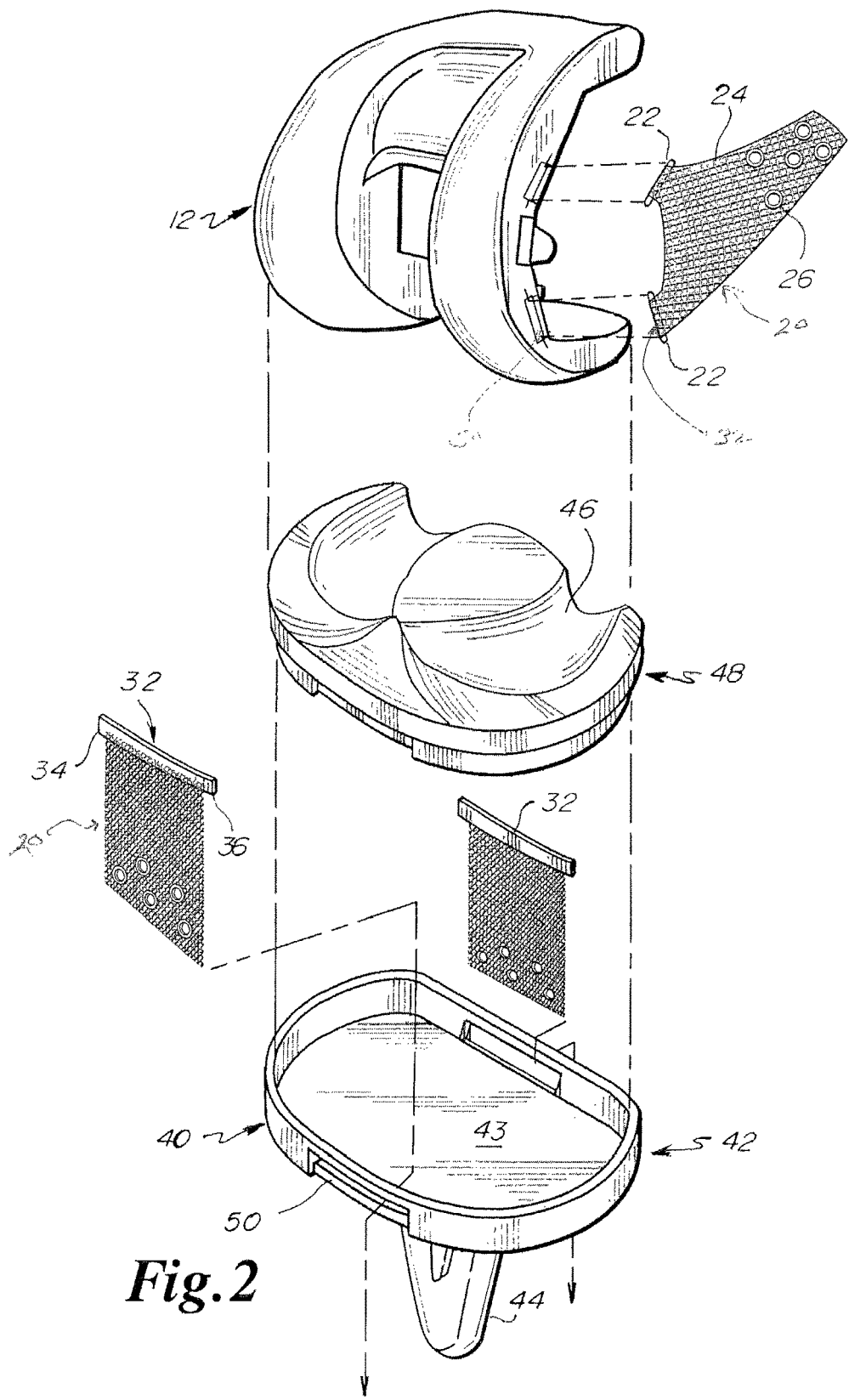
FIG. 2 is an exploded view of the total knee replacement implant and external bone anchor system.

As shown for example in FIG. 2, the implant components are modified to include slots 50 through the body of the implant components. The tibial implant component 16 typically includes a base plate 40 and a tibial platform 42 with one or more stabilizing projections 44. A bearing surface 46 is formed on a liner 48 which is positioned on the distal surface of the base plate 40.

The base plate 40 is shown modified to have two slots 50 formed there through, one being anterior and the other posterior on the base plate as shown. The width of the slots 50 is less than the length of the enlarged rigid structure 32. Thus, the enlarged rigid structure may be held to the implant component by be positioned with the enlarged rigid structure 32 within the slot 50 such that the tabs 34, 36 prevent the flexible bone anchor 20 from passing there through.

Soft tissue bone anchors 30 are well known in the art and are shown in U.S. Pat. No. 8,114,127 to West, Jr.; U.S. Pat. No. 9,005,246 to Burkhart et al.; U.S. Pat. No. 8,109,969 to Green, the disclosures of which are all incorporated herein by reference. Soft tissue anchors are preferred in this application since they do not have some of the disadvantages over bone screws which may loosen over time and may not be intended for a permanent connection. The soft tissue bone anchors 20 herein may be any of the soft tissue to bone anchors known to one of skill in the art which can connect the flexible bone anchor 20 to cortical bone.

FIGS. 8 and 10 show a flexible bone anchor 20 secured to cortical bone by way of soft tissue anchors 30. The soft tissue anchors 30 have a threaded body 52 which is secured into the cortical bone and sutures 54 secured to the threaded body are connected to the cortical bone connection end 24 through formed openings 26 or through mesh if present. This secures the flexible bone anchor 20 to the cortical bone.

Depending on the implant body, the slots may need to be positioned to avoid body ligaments, muscles or the like. As shown in FIGS. 3-6, the implant connection end 22 may be angled such that the enlarged rigid structure 32 is not at right angles with the main body of the flexible bone anchor 20 which allows the cortical bone connection end 24 to be angled to avoid any obstruction.

FIGS. 1, 2 and 22 are shown where the flexible bone anchor 20 is formed with two enlarged rigid structures 32 each of which is inserted into a slot 50 formed in the femoral implant component 12. In this example, the slot 50 likely will not pass through the femoral implant component 12 and will simply be a cavity which is enlarged internally such that the tabs 34, 26 will prevent the enlarged rigid structure 32 from being able to leave the slot 50 once manipulated inside the slot cavity. Although the implant connection end 24 of the flexible bone anchor 20 is shown with one or two ends it simply illustrates that the cortical bone connection end 24 may be formed with one or more enlarged rigid structures 32 such that it may be attached to the implant as needed to provide better strength or to avoid body structures for placement.

For placement of the flexible bone anchors 20, the implant connection end 22 is typically secured first to the implant. It may be slid through the slot 50 from behind such that the cortical bone connection end 24 is now to the outside of the implant where it may be positioned against cortical bone and secured with soft tissue bone anchors 30. Alternatively, if the implant cannot be formed with a slot that has access from an interior, the enlarged rigid structure 32 may be tilted at an angle such that the tabs 34, 36 are able to enter the slot 50 and pass through the slot into an enlarged cavity behind the slot shaped to accommodate the entire enlarged rigid structure 32 while captively and permanently holding it thereto.

FIG. 9 shows a form of the invention in which the knee base plate 40 is formed with two opposing slots 50, with one to the anterior and the other to the posterior. In such a form, the flexible bone anchor 60 can be formed with two cortical bone connection ends 24 such that the main body of the flexible bone anchor 60 passes through the slots and each end 24 is secured to cortical bone via a soft tissue bone anchor 30. This is possible in some locations but is more difficult in other areas due to body structures that may be in the way of such an approach.

Figure 11:
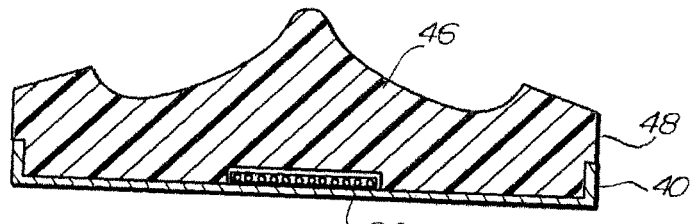
FIG. 11 is sectional view of the tibial implant component showing the flexible bone anchor.

FIG. 8 shows a cross-section of a flexible bone anchor 20 secured to a resected tibia 18 and soft tissue bone anchors 30. FIG. 11 shows a cross-sectional view through the implant base plate 40, liner 48 and flexible bone anchor 20 to show how it resides in the slot 50. FIG. 10 shows a similar view to FIG. 8 where the slot 50 doesn't have a bottom raised lip 62.

Figure 12:
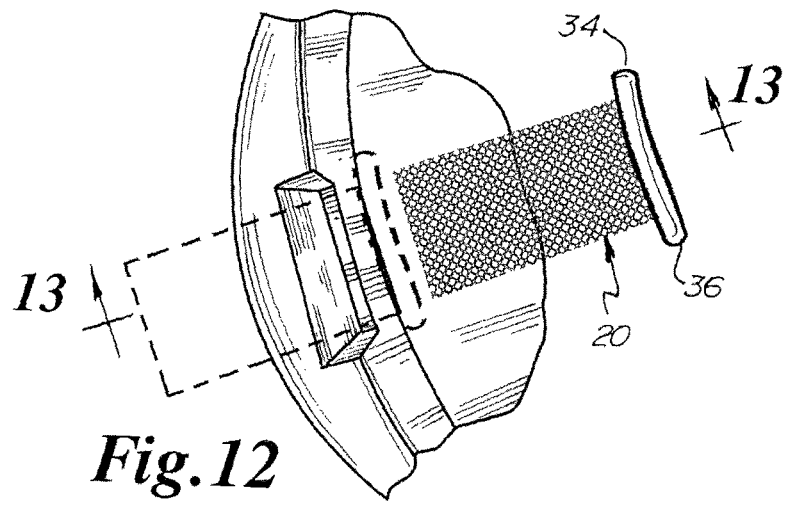
FIG. 12 is a view of a flexible bone anchor being inserted into a slot in a tibial implant component.
Figures 13, 14:
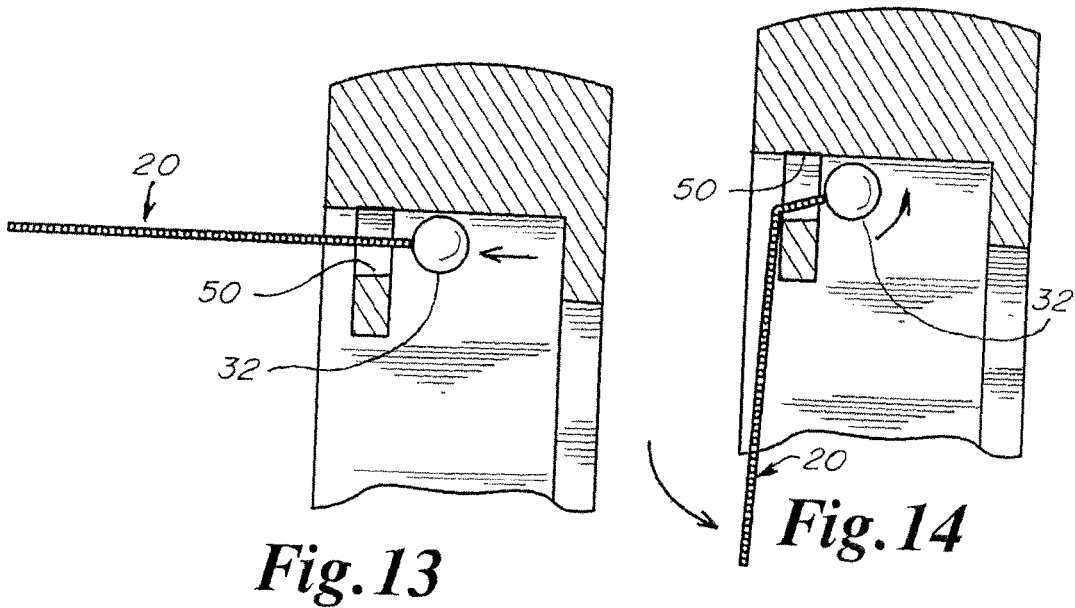
FIG. 13 is a view showing the flexible bone anchor in a slot in a tibial implant component.
FIG. 14 is a view of the flexible bone anchor of FIG. 13 moved downward to be positioned adjacent tibial bone.

FIGS. 12-14 show the insertion of a flexible bone anchor 20 such that its implant connection end 22 is held to an implant within a slot 50. FIGS. 13 and 14 show how the enlarged rigid structure 32 may be pulled against slot 50 and then the flexible bone anchor 20 may be pulled down toward the cortical bone for affixation which readily shows how the implant connection end 22 is held permanently to the new implant.

For total hip replacement surgery, the invention is also used to assist the strength of the new joint by providing a connection between the new implant and external cortical bone. Many manufacturers currently produce stem portions which are inserted into a resected femur and a new ball portion fits into an acetabular socket which may be reformed with plastic, metal or combinations.

After the femur has been resected and the new stem has been inserted into an opening formed in the femur, the new joint may be stabilized by addition of one or more of the flexible bone anchors of the invention.

FIG. 15 shows a typical total hip replacement in which the upper end of a resected femur 64 has been fitted with a hip stem 66 that includes a ball 70 that replaces the head of the femur and a shell 72 that lines the acetabulum (hip socket). A flexible bone anchor 20 is shown secured to the cortical bone of the resected femur 64 and to the hip stem 66.

Figure 18:
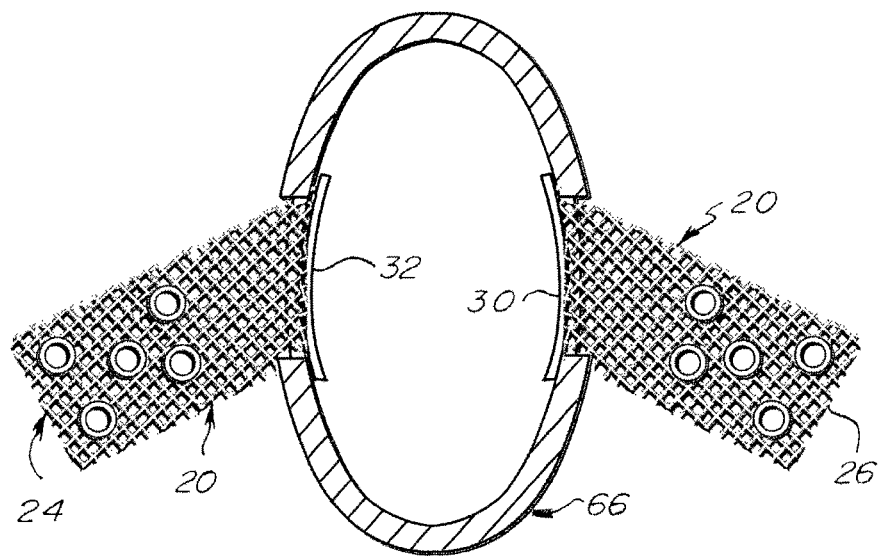
FIG. 18 is a cross-sectional view similar to FIG. 17 in which the flexible bone anchors are angled.
Figure 19:
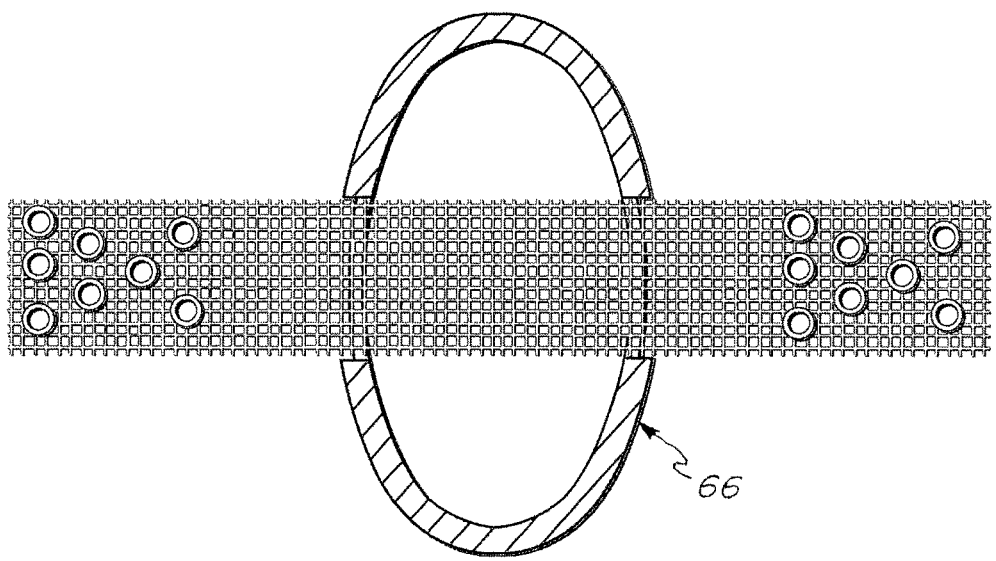
FIG. 19 is a cross-sectional view through a hip stem showing an alternative design in which a single flexible bone anchor could be used that passes through the hip stem.

FIG. 16 shows just the hip stem 66 that has been formed with an opening 76 as best shown in FIGS. 17-19 in which the enlarged rigid structure 32 of the flexible bone anchor 20 may be inserted and locked thereto. As shown in FIG. 17, the flexible bone anchor 20 may be inserted and locked into the hip stem opening 76 by angling in first one tab 34 and then the remainder of the enlarged rigid structure until the other tab 36 passes through the opening 76 into the space beyond the formed hip stem opening 76. A straight pull back on the flexible bone anchor 20 will lock it against the smaller opening forming a permanent connection once the cortical bone connection end 24 is secured via soft tissue bone anchors 30 to the resected femur 64.

FIG. 18 again shows that the flexible bone anchors may be formed such that an angle is made between the main body of the titanium mesh compared to the enlarged rigid structure 32. This allows the flexible bone anchor 20 to be situated wherever desired on the cortical bone of the repaired joint.

FIG. 19 shows an alternative embodiment in which a flexible bone anchor 60 passes through two hip stem openings 76 such that it is held to the implant and both cortical bone connection ends 24 may be secured to cortical bone of the resected femur 64 via soft tissue bone anchors 30.

This completes the description of the preferred and alternate embodiments of the invention. Those skilled in the art may recognize other equivalents to the specific embodiment described herein which equivalents are intended to be encompassed by the claims attached hereto. For example, while the drawings show the invention in connection with hip and knee implants, it may be used in any animal joint needing an implant including shoulders and elbows.

The invention claimed is:

1. An external bone anchor for use with animal joint implants comprising:
    (a) a flexible bone anchor formed as a non-absorbable sheet having a cortical bone connection end and an implant connection end, with a portion of said sheet being shaped to conform to a cortical bone surface adjacent said animal joint implant;
    (b) said implant connection end of said flexible bone anchor including an implant connection member configured to make a permanent connection to said animal joint implant, said implant connection member includes an elongated rigid structure having a thickness substantially greater than a thickness of the sheet which is locked into a recess formed in said joint implant, said recess adjacent to a slot in said animal joint implant for receiving said elongated rigid structure;
    (c) said cortical bone connecting end including openings through which soft tissue anchors may be attached to secure the bone anchor to cortical bone adjacent said joint implant; and
    (d) soft tissue anchors for securing the bone anchor to cortical bone through said cortical bone connecting end openings to thereby supply rigid fixation between the cortical bone and the joint implant.

2. The external bone anchor of claim 1 wherein said flexible bone anchor is formed from titanium.

3. The external bone anchor of claim 1 wherein said flexible bone anchor is formed from non-absorbable suture material woven into a mesh.

4. The external bone anchor of claim 1 wherein said soft tissue anchors include at least one threaded body secured into cortical bone and said flexible bone anchor is secured to said soft tissue anchors via tied sutures secured at said cortical bone connecting end openings.

5. An external bone anchor system for use with animal joint implants comprising:
    (a) a flexible bone anchor formed of a non-absorbable sheet having a cortical bone connecting end and an implant connection end, with the cortical bone connecting end being shaped to conform with an underlying cortical bone surface;
    (b) said implant connection end of said flexible bone anchor including an implant connection member configured to make a permanent connection to said animal joint implant, with the implant connection member being an elongated structure and having a thickness substantially greater than a thickness of the sheet;

(c) an animal joint implant including at least one slot recess into which said implant connection member may be inserted and secured;

(d) said cortical bone connecting end including openings through which soft tissue anchors may be attached to secure the external bone anchor to cortical bone adjacent said joint implant; and (e) soft tissue anchors for securing to cortical bone through said cortical bone connecting end openings to thereby supply rigid fixation between the cortical bone and the joint implant.

6. The external bone anchor of claim 5 wherein said flexible bone anchor is formed from titanium.

7. The external bone anchor of claim 5 wherein said flexible bone anchor is formed from non-absorbable suture material woven into a mesh.

8. The external bone anchor of claim 5 wherein said soft tissue anchors includes at least one threaded body and said flexible bone anchor is secured to said soft tissue anchors via sutures tied between said cortical bone connecting end openings and said soft tissue anchors.

* * * * *